(12) United States Patent
Ernst et al.

(10) Patent No.: US 9,234,836 B2
(45) Date of Patent: Jan. 12, 2016

(54) MEASUREMENT OF A FIBER DIRECTION OF A CARBON FIBER MATERIAL AND FABRICATION OF AN OBJECT IN CARBON FIBER COMPOSITE TECHNIQUE

(71) Applicant: Fraunhofer-Gesellschaft, Munich (DE)

(72) Inventors: Juergen Ernst, Erlangen (DE); Stephan Junger, Bubenreuth (DE); Wladimir Tschekalinskij, Nuremberg (DE)

(73) Assignee: Fraunhofer-Gesellschaft zur Foerderung der Angewandten Forschung e.V., Munich (DE)

( * ) Notice: Subject to any disclaimer, the term of this patent is extended or adjusted under 35 U.S.C. 154(b) by 0 days.

(21) Appl. No.: 13/677,917

(22) Filed: Nov. 15, 2012

(65) Prior Publication Data

US 2014/0132947 A1    May 15, 2014

(51) Int. Cl.
*G01J 3/00* (2006.01)
*G01N 21/21* (2006.01)

(52) U.S. Cl.
CPC ..................................... *G01N 21/21* (2013.01)

(58) Field of Classification Search
CPC ...................................................... G01B 11/00
USPC ........... 356/445–448, 238.1–238.3, 364–370, 356/237.1–237.2, 33, 34, 35, 51
See application file for complete search history.

(56) References Cited

U.S. PATENT DOCUMENTS

| | | | | |
|---|---|---|---|---|
| 4,201,815 A * | 5/1980 | Weiland et al. | | 428/113 |
| 4,818,612 A * | 4/1989 | Hara et al. | | 428/367 |
| 5,317,387 A * | 5/1994 | Van Hengel et al. | | 356/625 |
| 5,974,896 A * | 11/1999 | Manzouri | | 73/800 |
| 6,091,499 A * | 7/2000 | Abraham | | G01B 11/26 356/369 |
| 6,535,286 B1 * | 3/2003 | Green et al. | | 356/369 |
| 6,559,942 B2 * | 5/2003 | Sui | | G01N 21/21 257/E21.252 |
| 6,624,883 B1 * | 9/2003 | Zhou | | G01B 11/30 250/559.25 |
| 7,186,968 B2 * | 3/2007 | Raynor | | 250/225 |
| 7,265,834 B2 * | 9/2007 | Kawakami et al. | | 356/364 |
| 7,433,031 B2 * | 10/2008 | Xu et al. | | 356/237.2 |
| 2004/0012853 A1 * | 1/2004 | Garcia et al. | | 359/485 |
| 2004/0233434 A1 * | 11/2004 | Wang | | 356/365 |
| 2008/0212895 A1 * | 9/2008 | Mattox | | 382/294 |
| 2008/0297783 A1 * | 12/2008 | Urano et al. | | 356/237.5 |
| 2009/0101297 A1 * | 4/2009 | Jez et al. | | 162/198 |
| 2009/0296088 A1 * | 12/2009 | Smith | | 356/367 |

(Continued)

FOREIGN PATENT DOCUMENTS

| | | |
|---|---|---|
| FR | 2 391 070 A1 | 12/1978 |
| GB | 1 567 367 A | 5/1980 |
| WO | 2007/070306 A2 | 6/2007 |

(Continued)

OTHER PUBLICATIONS

David Lara, "Double-pass axially resolved confocal Mueller matrix imaging polarimetry", Nov. 1, 2005.*

(Continued)

*Primary Examiner* — Gregory J Toatley
*Assistant Examiner* — Maurice Smith
(74) *Attorney, Agent, or Firm* — Keating & Bennett, LLP

(57) ABSTRACT

The fiber direction of a carbon fiber material of a test object is detected by means of the polarization direction of light reflected by the test object. If, for example, non-polarized light impinges upon carbon fibers, light reflected by the fibers is polarized in fiber direction.

14 Claims, 3 Drawing Sheets

(56) References Cited

U.S. PATENT DOCUMENTS

2010/0110427 A1* 5/2010 Amary et al. .............. 356/302
2010/0208238 A1* 8/2010 Wilcken .................... 356/51

FOREIGN PATENT DOCUMENTS

WO 2009/112174 A1 9/2009
WO 2012/022972 A2 2/2012

OTHER PUBLICATIONS

Pejhman Ghassemi "Out-of-plane Stokes imaging polarimeter for early skin cancer diagnosis", Jul. 2012 SPIE.*
International Search Report issued in corresponding International Application PCT/EP2013/073719, mailed on Mar. 13, 2014.
Dlugunovich, et al., "Reflective Properties of Carbon-Fiber-Reinforced Plastic Heated in Air by Continuous Radiation from a CO2 Laser," High Temperature, vol. 28, No. 6, Nov. 1990, pp. 860-863.

* cited by examiner

MEASUREMENT OF A FIBER DIRECTION OF A CARBON FIBER MATERIAL AND FABRICATION OF AN OBJECT IN CARBON FIBER COMPOSITE TECHNIQUE

BACKGROUND OF THE INVENTION

The present invention relates to a concept for measuring a fiber direction of a carbon fiber material, like for example for quality testing and/or further processing and for a manufacturing of an object in a carbon fiber composite construction.

In modern lightweight construction, more and more carbon fibers are used for increasing the strength of so-called carbon fiber composite materials. In particular with safety-critical members made of these composite materials, like e.g. in aircraft construction, automobile construction or the like the correct position and the correct course, i.e. the direction of the carbon fibers are of decisive importance for the mechanical strength and load capacity of the complete member. At any point or at any relevant points of the work piece, it is a need to measure the fiber course or the angle in which the carbon fibers are positioned with a certain accuracy. Conventionally, in manufacturing several layers of carbon fiber fabrics are stacked, one after the other on top of each other and each soaked with special plastics and hardened or cured. Each of these layers has to be qualified with respect to the fiber course. As the carbon fiber layers are non-transparent for visible light, testing the fiber direction has to be executed individually for each layer each after depositing the layer.

Until now, the fiber direction has been measured or controlled in different ways, i.e. a) visually by the production staff, b) by depositing marks by the production staff, detecting the marks by means of a camera system and further processing the camera images by a corresponding software, and c) by recording the carbon fibers using a camera system whose pixel resolution has to be so high, however, that the individual carbon fibers are visually resolved so that from the image data by means of a special software the direction of the carbon fibers may be determined in any place of the image.

Solutions a) and b) need the help of the production staff and are thus difficult to reproduce and error prone due to the known subjective effects. Apart from that, the solutions are time-consuming and thus expensive. A completely automated testing is not possible. Solution c) needs a comparatively high pixel resolution of the used camera. Apart from higher costs for a camera with a high resolution, with higher pixel numbers more image data result, which leads to a higher image transmission speed and a higher computing power for image evaluation at the same bitrate. A higher data rate and high computing power again lead to higher costs. On the other hand, this means that with a certain expenditure the testing speed is limited. Finally, this means that for testing a certain area of a carbon fiber composite member, acceptable costs determine the testing speed. A further disadvantage is the fact that the fiber direction has to be calculated by software from the image data. The accuracy and reliability of the results thus substantially depend on the quality of the software. In particular with fabric soaked by plastics, the detection of the fiber direction is substantially more inaccurate and less reliable than with a non-soaked so-called "textile" fabric.

Thus, a concept for measuring the fiber direction of a carbon fiber material would be desired or a concept for manufacturing an object in a carbon fiber composite construction which overcomes above mentioned disadvantages or enables a more cost-effective manufacturing with the same quality or accuracy.

SUMMARY

According to one embodiment, a device for measuring a fiber direction of a carbon fiber material of an object to be tested or device under test may comprise the following feature: a polarization sensor for detecting a polarization direction of light reflected by the object to be tested, wherein the polarization direction indicates the fiber direction.

According to a further embodiment, a system for manufacturing an object in carbon fiber composite construction may comprise the following features: a device for measuring a fiber direction of a carbon fiber sheet of a carbon fiber material of a test object having a polarization sensor for detecting a polarization direction of light reflected by the object to be tested, wherein the polarization direction indicates the fiber direction; and a manipulator for stacking the carbon fiber layers on top of each other by adjusting the fiber directions of the carbon fiber layers according to the measurement by the device.

According to a further embodiment, a method for measuring a fiber direction of a carbon fiber material of a test object may comprise the following steps: illuminating the test object or object to be tested; and detecting a polarization direction of light reflected by the test object, the polarization direction indicating the fiber direction.

A further embodiment may comprise a computer program having a program code for executing the inventive method for measuring a fiber direction of a carbon fiber material of a test object when the program is executed on a computer.

The present invention utilizes the finding that it is possible to detect the fiber direction of a carbon fiber material of a test object using the polarization direction of light reflected by the test object. If, for example, non-polarized light impinges upon carbon fibers, light reflected by the fibers is polarized in fiber direction. The wavelength of the light is for example in a range of 400 to 1000 nanometers.

It is possible to visually measure the fiber direction of the carbon fiber material, like e.g. a carbon fiber fabric or a carbon fiber composite material by means of the polarization of light. According to one embodiment, as a polarization sensor accordingly a polarization-sensitive camera is used which records the test object to acquire a spatially resolved detection of the polarization direction and thus a spatially resolved sampling of the fiber direction. Advantageously, it is not necessary for the resolution of the polarization-sensitive camera to suffice to optically resolve the fibers. In other words, the spatial resolution of the polarization-sensitive camera in the object plane of the lens or objective of the camera may be less than it would be needed to resolve the structure of the fibers on the surface of the carbon fiber material, i.e. the pixel repeat distance in the object plane of the lens may be greater than for example the fiber radius.

BRIEF DESCRIPTION OF THE DRAWINGS

In the following, embodiments of the present invention are explained in more detail with reference to the accompanying drawings, in which.

DETAILED DESCRIPTION OF THE INVENTION

Figure 1:
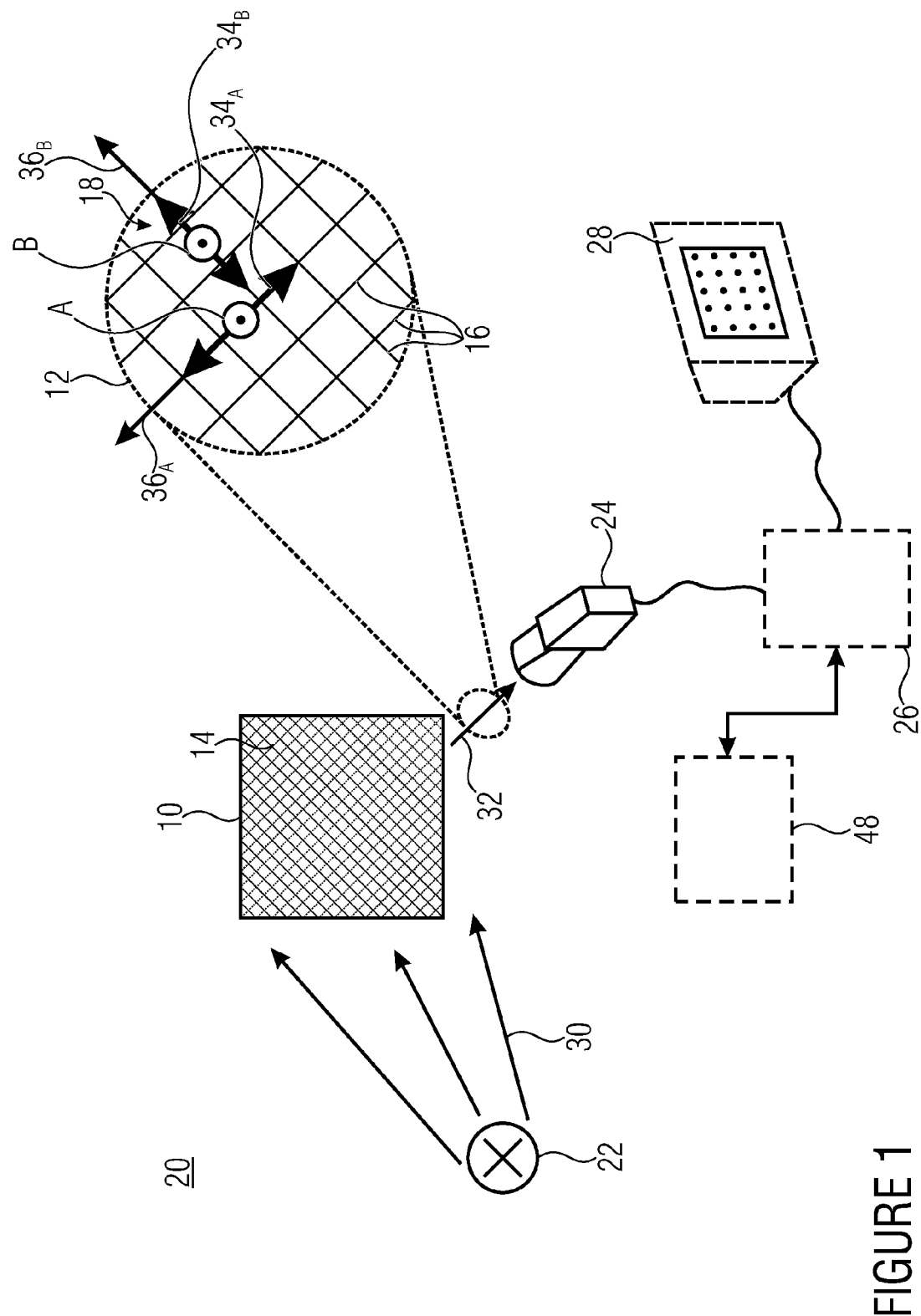
FIG. 1 is a schematical block diagram of a device for measuring a fiber direction of a carbon fiber material of a test object according to an embodiment of the present invention.

FIG. 1 shows a device for measuring a fiber direction of a carbon fiber material of a test object according to one embodiment of the present invention. The carbon fiber material may, for example, be a carbon fiber fabric as it is illustrated in FIG. 1 by the cross hatching. It may, however, also be a carbon fiber composite material. In FIG. 1, the test object 10 of the carbon fiber material is for example a sheet or a laminate of carbon fiber fabric which is, for example, provided to be applied after measuring to one or several other carbon fiber sheets in order to then also result in a carbon fiber composite. In this respect it is important to know the fiber directions of the carbon fiber material. The fiber direction may, however, also be needed for other reasons. In FIG. 1, in the dashed enlargement 12, as an example a view onto a front side 14 of the test object 10 and its carbon fiber material is illustrated. Therein, fiber bundles 16 are interwoven into a fabric 18. Alternatively, the object may be a stack of above-mentioned carbon fiber sheets—with or without plastics matrix, which may be cured or still uncured, i.e. it may be a product or intermediate product of a carbon fiber composite material.

The device for measuring the fiber direction of the carbon fiber material 18 of the test object 10 of FIG. 1 is generally designated by 20 and includes a light source 22, a polarization sensor 24 and optionally a computer 26 and optionally further a monitor 28. The light source 22 is implemented to illuminate the test object 10. The polarization sensor 24 is implemented to detect a polarization direction of light reflected by the test object 10, i.e. in particular light using which the test object was illuminated by the light source 22 and which is then reflected into the polarization sensor 24, wherein the polarization direction indicates the fiber direction of the object 10 at its illuminated front side 14.

In the assembled state, the light source 22 is thus aligned to illuminate the test object 10. The light 30 emitted by the light source 22 is for example non-polarized. It is for example a halogen lamp, thermionic lamp, LED or the like. Simultaneously, several lamps of the same or a different type may illuminate the object 10 from different directions or with the help of other devices like mirrors, optical fibers or the like an illumination from several directions may be realized, i.e. the light source may comprise several lamps and/or additional light guiding means, like e.g. mirrors, etc. in order to realize an illumination of the object 10 from different directions and to thus acquire a more complete illumination of the surface 14 sampled by the polarization sensor 24 or facing the same, i.e. preventing shadowings, etc. The light spectrum of the light 30, like e.g. its average wavelength, is for example in a range from 400 to 1000 nm. In particular, the light source 22 may be a wide band or narrowband light source. It is also possible to use a monochromatic light source 22. Advantageously, a half-width of the spectrum of the light source 22 is in a range smaller than or equal to 100 nm.

As soon as the light 30 impinges upon the test object 10, the advantageous characteristic of the carbon fiber material 18 has a positive effect, according to which the latter is polarizing for light impinging upon the same. In particular, light 30 is polarized after its reflection at the carbon fiber material of the test object 10 along a polarization direction which passes along the fiber direction at the illuminated surface 14. In the enlarged section 12, which shows a top view onto a section of the surface 14 of the object 10 from the direction of the polarization sensor 24, this is exemplarily illustrated for two different positions A and B of the test object. The light 32 reflected at position A and impinging upon the polarization sensor 24 comprises a polarization direction $34_A$ which passes in parallel to the fiber direction $36_A$ of the fiber bundle 16 which crosses position A. At position B, the fiber direction $36_B$ and thus also the polarization direction $34_B$ which passes in parallel to the same runs in a different direction, i.e. perpendicular to the direction $36_A$ or $34_A$, as position B is exemplarily located at a different fiber bundle 16.

The polarization sensor 24 may be one which only measures the fiber direction of the carbon fiber material 10 pointwise across the polarization direction of light 32 reflected at this point or may be a line or area sensor or a polarization-sensitive camera. In the first case mentioned, if it is desired, for a spatially resolved sampling of the fiber direction for example a manipulator or a robot (not illustrated) may be used to laterally shift or vary the point or location sampled by the polarization sensor 24 from which reflected light is detected by the polarization sensor 24 and to thus acquire corresponding fiber direction measurements at different positions A and B.

Figure 2:
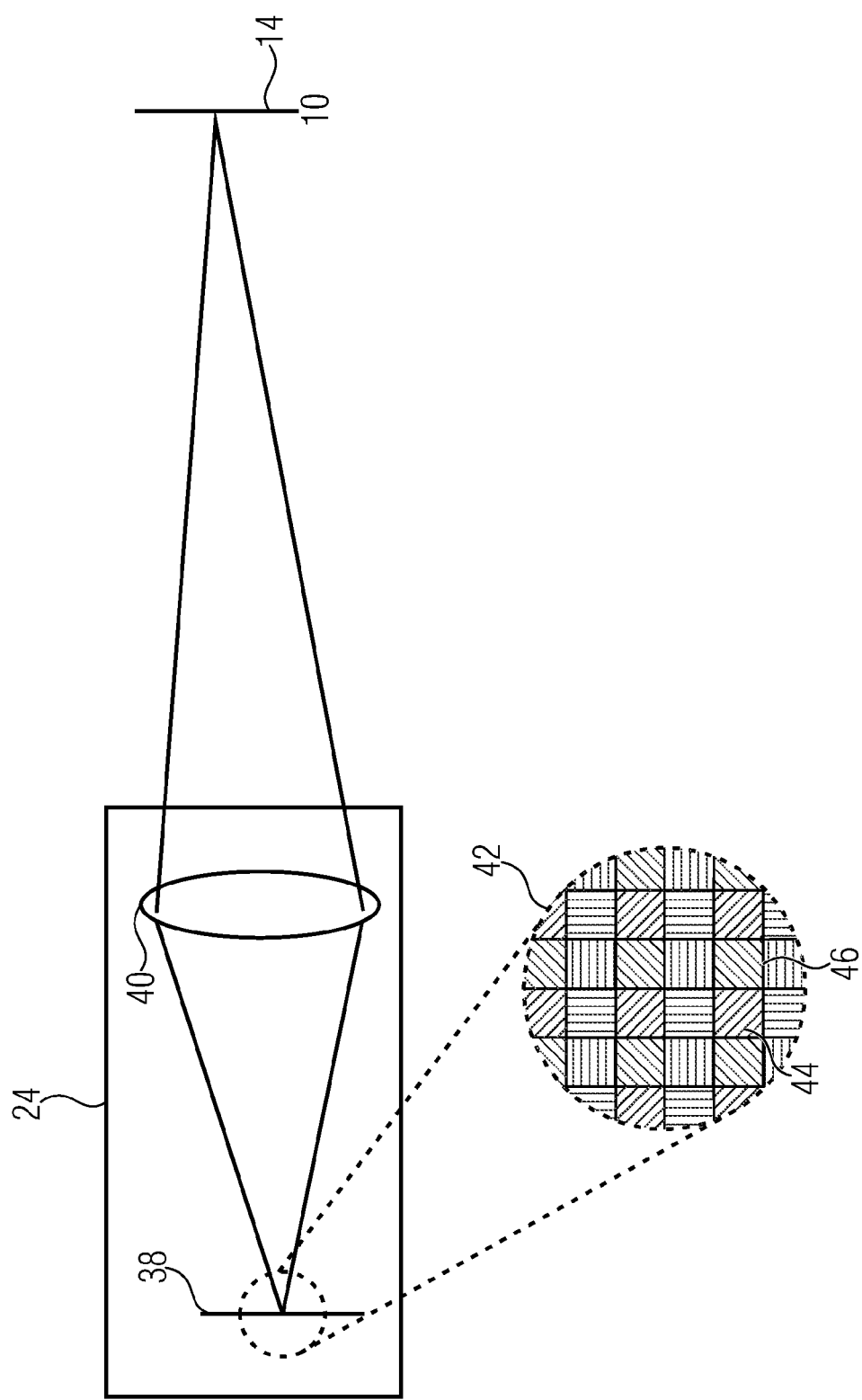
FIG. 2 is a schematical illustration of a polarization-sensitive camera functioning as a polarization sensor according to one embodiment.

FIG. 2 shows that the polarization sensor 24 may be a polarization-sensitive camera. According to this embodiment, the polarization-sensitive camera 24 includes a pixel array 38 and an objective 40 for imaging the test object 10 onto the pixel array 38. As illustrated in the enlarged top view 42 onto the pixel array 38 in FIG. 2, the pixels 44 of the pixel array 38 may for example be grouped into super-pixels 46, so that the super-pixels 46 each comprise pixels 44 of the pixel array 38 which are sensitive with respect to differently polarized light, i.e. at least a first pixel for a first polarization direction and a second pixel for a second different polarization direction. FIG. 2 exemplarily illustrates that each super-pixel 46 for example comprises four pixels 44 which are sensitive with respect to polarization directions spaced apart from each other by 40° angle differences. Another number of pixels with a different polarization sensitivity is of course also possible, just like a non-equiangular distribution of the polarization directions of those pixels. It is to be noted that it is not important whether, as illustrated in FIG. 2, the pixels are arranged regularly in lines and columns, in a different regular arrangement or irregularly, or whether the arrangement of the pixels within the super-pixels 46 is the same or whether the arrangement of the pixel sensitive to the different polarization directions within the super-pixels 46 varies across the pixel array 38. It is likewise possible for the super-pixels 46 not to be arranged regularly in line and column direction but the same may also be arranged differently in a regular or irregular way.

Sampling by the polarization sensor 24 is not limited to a point or area sampling, as described above. It would also be possible to execute a sampling in lines or a one-dimensional sampling of the fiber direction of the carbon fiber material of the test object 10 at the illuminated front side 14. Also here, a relative movement between object 10 and polarization sensor 24 may be used to all in all acquire a two-dimensional sampling of the fiber direction.

The polarization sensor 24 may further comprise a filter system to filter out light of a certain wavelength from the reflected light 32, like e.g. the light of a wavelength in the above mentioned range between 400 to 1000 nm. The pixel array 38 may, for example, comprise an array of light-sensitive areas above which again an array of filter structures is located, so that each light-sensitive area together with a filter structure results in a pixel. The filter structures upstream from the individual light-sensitive areas may, for example, be grid structures. It would in particular be possible for the filter structures to comprise structure elements having dimensions within the sub-wavelength range, i.e. smaller than the wavelength of light 30. The filter structures may comprise characteristics of a photonic crystal. Light-sensitive areas and filter structures may together be integrated in a chip. The light-sensitive areas may, for example, be formed by a photodiode array, a CCD array or a CMOS pixel array. Such a polarization sensor is for example described in DE 102008014334.

The polarization sensor 24 may also consist of a conventional CCD or CMOS image sensor, i.e. a sensor which is not sensitive to polarization, i.e. a single, line or image sensor, and a device arranged between the sensor and the object 10 for a continuous or gradual rotation of the polarization direction of light 32, i.e. a polarization filter whose pass-through polarization direction is temporally varying. The device for rotating the polarization direction of light or the polarization filter with a varying pass-through polarization direction enables, one after the other, i.e. sequentially in time, to record several images and to combine the same in a suitable way in order to this way acquire the local polarization angle at each location of the surface 14.

As it was illustrated in FIG. 1, the device 20 may optionally comprise a computer 26 and a display device 28. The computer 26 may for example be provided to convert the pixel values of the super-pixels in a case of an implementation of the polarization sensor 24 as an area sensor into suitable scalar values, i.e. one or several per super-pixel, which are among others a measure for the local polarization angle of the reflected light 32 at the location of the surface 14 associated with the super-pixel or for the fiber direction at this location. On the display device, the spatially resolved sampling of the fiber direction may be displayed in a color-encoded way. The computer 26 or a program executed therein may further control the above-mentioned optionally existing manipulator 48 for generating a relative movement between object 10 and polarization sensor 24.

The computer 26 may in particular also act as a controller which determines the orientation of the fiber direction of the object 10 with respect to the shape or design of the object 10 from the fiber direction of the carbon fiber material of the object 10 determined via the polarization sensor 24 and position information regarding the object 10 and controls a manipulator depending on this orientation which holds the object, in other words, the controller may control a manipulator for holding and changing the position of the object depending on the position information on a position of the object 10 relative to the polarization sensor 24 and the fiber direction of the object, to control a manipulator for adjoining the object and another object so that in an adjoined or contacting state the fiber direction comprises a predetermined orientation relative to the other and/or depending on the position information regarding a position of the object 10 relative to the polarization sensor 24 and the fiber direction of the object, to determine an orientation of the fiber direction with respect to a design of the object 10. Contacting or adjoining may be executed so that the side 14 in a contacting state adjoins the other object, i.e. for example so that the fiber direction has a predetermined directional relation to a designated preferential direction of the corresponding facing side of the other object, like e.g. a carbon fiber direction, like e.g. transverse to the same. Of course the above mentioned manipulator may also be the one which holds the object at the position defined by the position information at the moment of detecting the polarization direction and thus the fiber direction. In the following, an example in this respect is described within the scope of a manufacturing system.

Figure 3:
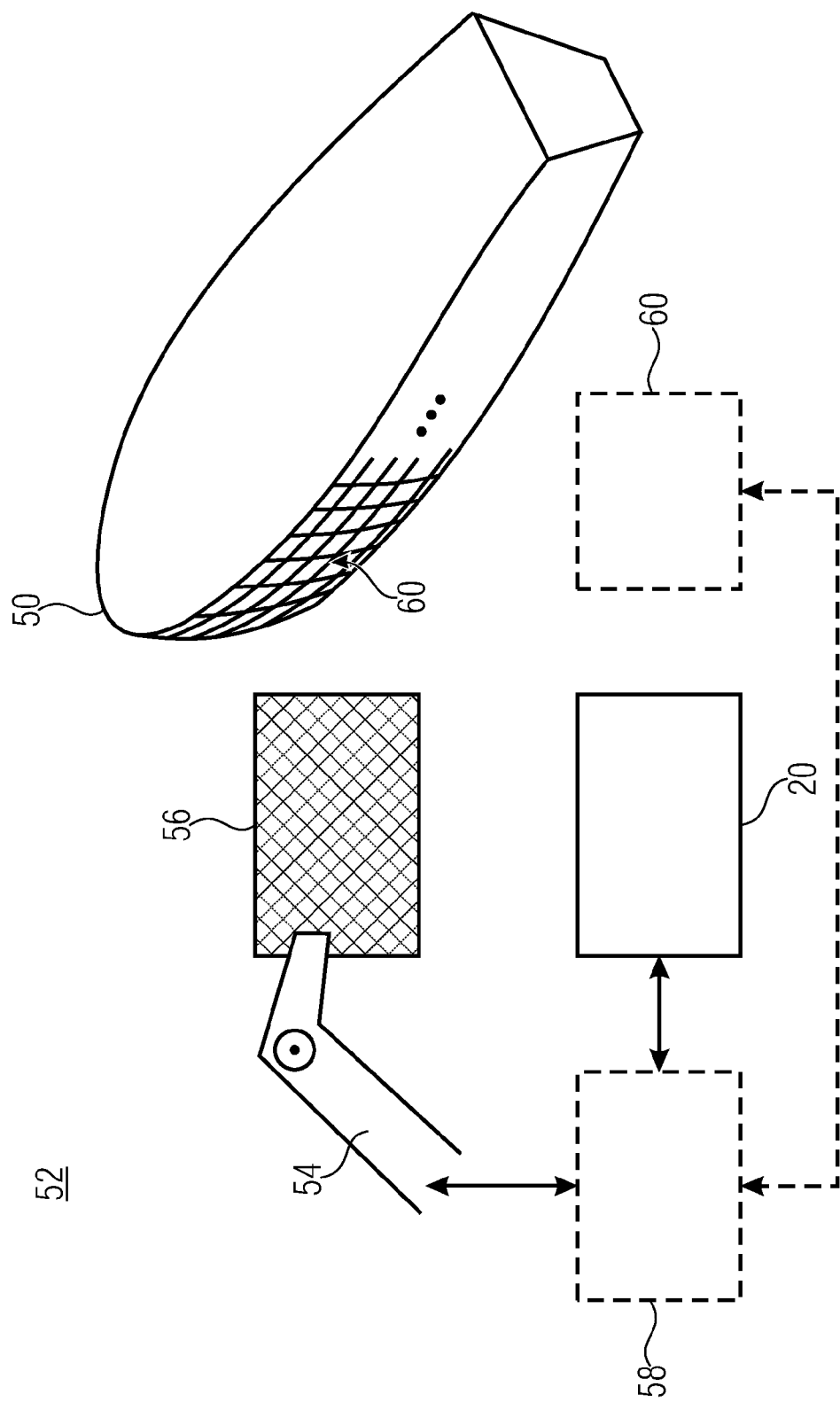
FIG. 3 is a block diagram of a system for manufacturing an object in a carbon fiber composite construction according to one embodiment.

FIG. 3 shows a system for manufacturing an object 50 in a carbon fiber composite construction according to one embodiment. The system generally designated by 52 uses or includes the device 20 of FIG. 1 and a manipulator or robot 54. As described, the device 20 executes the measurement of a fiber direction of carbon fiber layers 56. The robot 54 is implemented to spread the carbon fiber layers 56 adjusting the carbon fiber directions of the same with respect to each other according to the measurements by the device 20 in order to this way acquire the object 50. For example, a controller may be provided which controls the robot 54 and evaluates carbon fiber directions determined via the polarization direction of the reflected light.

The controller 58 would for example control the manipulator or robot 50 so that the device 20 may determine the fiber direction of the carbon fiber layer 56, i.e. that the object 10 is illuminated and in the focus of the polarization sensor 24. Knowing the position of the object relative to the polarization sensor when detecting the polarization direction and the detected polarization direction, the controller 58 would then get to know an orientation of the fiber direction relative to a shape or design of the object 10 and may for example control the robot 54 so that the current carbon fiber layer 56 is applied onto already super-positioned other carbon fiber layers 60 so that the fiber direction of the carbon fiber layer 56 to be currently applied forms a predetermined angle with the fiber direction of the currently exposed carbon fiber layer, which for example leads to an especially stable shape of the object 50. The object 50 may be, for example, as indicated in FIG. 3, the hull of a ship or a part of a body of an airplane or part of a motor vehicle.

A means 60 indicated in FIG. 3 by the dashed boxes 60 and, if applicable, also controlled by the controller 58 may be provided to provide the carbon fiber layers with plastics so that the carbon fiber layers are embedded in plastics, the so-called matrix, after a hardening or curing of the plastics. Providing the carbon fiber layers with plastics may be executed individually before respectively depositing the respective layer, individually each after depositing the respective carbon fiber layer or for several carbon fiber layers together in one step after stacking the same on top of each other.

An advantage of the above embodiments is the direct receipt of information via the fiber direction without being dependent on pattern recognition or the like. The measured polarization direction directly results in the fiber direction at the respective position of the test object and measurement may thus be executed quickly and reliably and in particular does not delay manufacturing in case of FIG. 3.

In other words, above embodiments are based on the fact that carbon fibers have the characteristic to partially reflect incoming light which is generally not polarized and to polarize here in parallel to the longitudinal fiber direction. This characteristic of polarizing behavior is utilized in the above embodiments to determine the fiber direction. In this respect, a visual measurement of polarization is used. By means of a device which is suitable for such a visual measurement, light reflected by the carbon fibers, like, e.g. a carbon fiber fabric, is analyzed with respect to the direction of the polarization direction. The result then directly represents the direction of the carbon fibers at the respective position. The device may be suitable for a visual, two-dimensional detection and analysis of the polarized light, as it was described with respect to FIG. 2, which shows a polarization-sensitive camera or a "polarization camera". According to some embodiments, the test object of carbon fibers is illuminated by a suitable light source, wherein a polarization camera is directed to the object. The polarization direction of the reflective light measured at every position of the object by the camera directly indicates the direction of the carbon fiber at this position. The wavelength of the light may, for example, be in a range from 400 to 1000 nm. As it was already indicated above, it is advantageously not necessary for the resolution of the camera to be so high that the fibers have to be detected individually in order to be able to calculate the direction of the fibers by software. To the contrary, the fibers themselves polarize the light in longitudinal fiber direction and the camera only has to be able to analyze the polarization in a spatially resolved way. This means that in case of FIG. 2 the pixel resolution of the camera may be clearly lower than in case of the method according to c) mentioned in the introductory part of the description of the present application. Due to the low data rate and low computational effort this leads to low system costs. Or in other words, in case of the above embodiments a larger area of carbon fibers may be tested in the same time at the same costs which leads to a higher number of pieces in routine piece tests and lower piece costs. A further aspect is the fact that the detection of the fiber direction is executed based on physical laws and not by calculations using software, which is why the detection of the fiber direction is substantially more secure. This in particular applies to fabric soaked with plastics where method c) from the introductory part of the description which was used up to now works relatively restrictedly and inaccurately.

In general, above embodiments may be used in many different fields of technology. For example, use in lightweight construction would be possible where carbon fibers are processed into so-called CFK (carbon fiber reinforced plastics) and quality of the products has to be guaranteed. Examples are aerospace, auto vehicle construction, wind power plants, etc.

Although some aspects have been described in connection with a device, it is obvious that those aspects also represent a description of the corresponding method, so that a block or a member of a device may also be regarded as a corresponding method step or as a feature of a method step. Analog to that, aspects which were described in connection with or as a method step also represent a description of a corresponding block or detail or feature of a corresponding device. Some or all of the method steps may be executed by a hardware apparatus (or using a hardware apparatus), like for example a microprocessor, a programmable computer or an electronic circuit. In some embodiments, some or more of the most important method steps may be executed by such an apparatus.

Without having noted this above, it may be the case that for example the computer 26 in FIG. 1 or another processing means determines a three-dimensional fiber direction or a fiber direction in an area parameterization of the surface 14 of the object 10 from the acquired polarization direction which indicates the polarization direction two-dimensionally in a projection along the direction along which the reflected light impinges upon the polarization sensor 24, by allocating a place in a parameterization of the surface 14 of the object 10 to the detected polarization direction and determining the fiber direction so that it is in this point tangential to the surface 14 and lies within the plane which is spanned by the direction of the reflected light and the determined polarization direction. Of course, one may also see to the fact that the surface 14—for example at least at the currently sampled location—is aligned basically perpendicular to the direction of the reflected light and the determined polarization direction. Of course, one may also see to the fact that the surface 14—for example at least at the currently sampled location—is basically aligned perpendicular to the direction of the reflected light.

Hitherto, above embodiments concentrated on the measuring of fiber directions and utilizing the thus gained information for purposes of handling the alignment of the object with respect to other objects. It is, however, additionally or alternatively possible to use the information for other purposes, like e.g. for purposes of quality control. The polarizing effect of carbon fibers onto reflected light may be used to test the direction of the carbon fibers during manufacturing carbon fiber reinforced members and compare the same to given values. This test may be executed but only with intermediate products, like e.g. the individual carbon fiber layers, but also with respect to complete members. It may in particular be tested whether the angles of the carbon fibers in the member or object have a mandatory value at each position of the member or whether the mutual alignment of the fibers in a fabric comprises a mandatory angle value at each provision.

Thus, in FIG. 1, the computer 26 may also function as an analysis means, like e.g. by a corresponding software executed thereon, and the device 20 may represent a quality measurement device. The analysis means may test whether the determined fiber direction fulfills a default condition in order to, in case of yes, classify the object 10 as being of a sufficient quality, and in case of no, classify the object 10 as not being of a sufficient quality. Depending on the result, the analysis means may cause a manipulator to transport the object 10 to a position A for rejected objects or to a position B, like e.g. an assembly position.

Testing whether the predetermined condition is fulfilled is, for example, provided by comparing the fiber direction at a position of the surface 14 of the object to a neighboring position, like e.g. testing whether the angle between the two directions lies in a predetermined angle range. Evaluation may also be executed statistically: a histogram of fiber directions at sampled positions of the surface of the object is generated and tested statistically. For example, two modes are determined and it is tested, whether the angle distance between the two modes lies in a predetermined range.

Testing whether the predetermined condition is fulfilled may, however, additionally or alternatively consider a characteristic surface direction of the object 10, like e.g. an edge, a main curvature or a perimeter of the surface 14. It may then be tested whether the fiber direction lies in a predetermined angle range relative to the characteristic surface direction. The characteristic surface direction may be detected automatically by the analysis means by pattern recognition or detection. The automatic detection may, in particular, be executed using a polarization-independent recording of the object 10. In case of using a camera as part of the polarization sensor 24 this is easily possible.

Finally, it is noted with respect to the above embodiments that it may also be the case that the light source is not part of the device or the system, but possibly part of the environment. Expressed in other words, the ambient light itself may be used. As described above, the assessment or evaluation of the polarizing effect may still be restricted to a wavelength range, like e.g. the above indicated advantageous wavelength range in which the light reflected by the object is not only divided in the polarization sensor with respect to its polarization, but is also filtered spectrally. The passband of the spectral filter may in particular be in a range between 400 and 1000 nm and have a half width of smaller or equal 100 nm.

Depending on the determined implementation requirements, embodiments of the invention may be implemented in hardware or in software. This in particular applies to the above-mentioned processing means, controllers, analysis means, etc. The implementation may be executed using a digital storage medium, for example a floppy disc, a DVD, a Blue-ray disc, a CD, an ROM, a PROM, an EPROM, an EEPROM or a flash memory, a hard disc or another magnetic or optical memory on which electronically readable control signals are stored which may cooperate or cooperate with a programmable computer system such that the respective method is executed. Thus, the digital storage medium may be computer-readable.

Some embodiments according to the invention thus include a data carrier comprising electronically readable control signals which are able to cooperate with a programmable computer system such that one of the methods described herein is executed.

In general, embodiments of the present invention may be implemented as a computer program product having a program code, wherein the program is operative to execute one of the methods when the computer program product is executed on a computer.

The program code may, for example, also be stored on a machine-readable carrier.

Other embodiments include the computer program for executing one of the methods described herein, wherein the computer program is stored on a machine-readable carrier.

In other words, one embodiment of the inventive method is thus a computer program comprising a program code for executing one of the methods described herein, when the computer program is executed on a computer.

A further embodiment of the inventive method is thus a data carrier (or a digital storage medium or a computer readable medium), on which the computer program for executing one of the methods described herein is recorded.

A further embodiment of the inventive method is thus a data stream or a sequence of signals which represent the computer program for executing one of the methods described herein. The data stream or the sequence of signals may for example be configured so as to be transferred via a data communication connection, for example via the internet.

A further embodiment includes a processing means, for example a computer or a programmable logics device which is configured or adapted to execute one of the methods described herein.

A further embodiment includes a computer on which the computer program for executing one of the methods described herein is installed.

A further embodiment according to the invention includes a device or a system which is configured to transfer a computer program for executing at least one of the methods described herein to a receiver. Transmission may be executed electronically or optically. The receiver may for example be a computer, a mobile device, a memory device or a similar device. The device or the system may for example include a file server for transferring the computer program to the receiver.

In some embodiments, a programmable logics device (for example a field programmable gate array, an FPGA) may be used to execute some or all functionalities of the methods described herein. In some embodiments, a field programmable gate array may cooperate with a microprocessor in order to execute one of the methods described herein. In general, the methods are in some embodiments executed by any hardware device. The same may be a universally usable hardware, like a computer processor (CPU) or hardware which is specific for the method, like for example an ASIC.

The above described embodiments merely represent an illustration of the principles of the present invention. It is obvious that modifications and variations of the arrangements and details described herein are obvious to other persons skilled in the art. It is thus desired for the invention to only be restricted by the scope of the following patent claims and not by specific details presented herein with respect to the description and the specification of the embodiments.

Although this invention was described with respect to several embodiments, there are changes, permutations and equivalents which are within the scope of this invention. It is further to be noted that there are many alternative types for implementing the methods and combinations of the present invention. It is thus desired for the following appended claims to be interpreted as including all such changes, permutations and equivalents which are part of the true nature and scope of the present invention.

The invention claimed is:

1. A device, comprising:
   a polarization sensor arranged to detect a polarization direction of light reflected by a carbon fiber material of an object, the polarization direction indicating a fiber direction of the carbon fiber material of the object;
   the polarization sensor includes a polarization-sensitive camera arranged to record the object to acquire a spatially resolved detection of the polarization direction and a spatially resolved sampling of the fiber direction of the carbon fiber material of the object; and
   the device further includes a controller configured and programmed to control a manipulator to position the object and another object next to each other depending on position information on a position of the object relative to the polarization sensor and the fiber direction of the carbon fiber material of the object, so that in an adjoined state the fiber direction of the carbon fiber material of the object comprises a predetermined orientation with respect to the other object.

2. The device according to claim 1, further comprising a light source for illuminating the object.

3. The device according to claim 2, wherein the light source is arranged to illuminate the object with light lying within a range between 400 and 1000 nm.

4. The device according to claim 1, wherein:
   the polarization-sensitive camera includes a pixel array and an objective configured to image the object onto the pixel array, and
   pixels of the pixel array are grouped into super-pixels so that each super-pixel includes pixels of the pixel array that are sensitive with respect to different polarization directions.

5. The device according to claim 4, wherein:
   each pixel includes a photo-sensitive area and a polarization filter structure upstream from the photo-sensitive area, and
   the filter structure includes a grid or structure elements with dimensions in the sub-wavelength range.

6. The device according to claim 1, wherein the device is configured to output the spatially resolved sampling of the fiber direction in a color encoded way.

7. The device according to claim 1, further comprising a spectral filter arranged to spectrally filter the light reflected by the object whose polarization direction is detected by the polarization sensor.

8. The device according to claim 7, wherein a passband of the spectral filter lies within a range between 400 and 1000 nm.

9. The device according to claim 1, further comprising a controller configured and programmed to control a manipulator to hold and change the position of the object depending on position information with respect to a position of the object relative to the polarization sensor and on the fiber direction of the object.

10. The device according to claim 1, wherein the light source is arranged to illuminate the test object with non-polarized light.

11. A system for manufacturing an object, comprising:
  a device configured to measure a fiber direction of each of a plurality of carbon fiber layers, comprising:
    a polarization-sensitive camera configured to detect, for each of the plurality of carbon fiber layers, a polarization direction of light reflected by the respective carbon fiber layer, the polarization direction indicating the fiber direction of the respective carbon fiber layer; and
  a robot configured and programmed to place the carbon fiber layers on top of each other depending on position information on a position of each of the plurality of carbon fiber layers relative to the polarization-sensitive camera and the fiber direction of each of the plurality of carbon fiber layers, so that in an adjoined state the fiber directions of the plurality of carbon fiber layers are in a predetermined orientation with respect to each other.

12. The system according to claim 11, further comprising a plastic application device configured to provide the carbon fiber layers with plastics, so that the carbon fiber layers are embedded into plastics after a curing of said plastics.

13. A method, comprising:
  illuminating carbon fiber material of a test object; and
  detecting, by a polarization-sensitive camera, a polarization direction of light reflected by the test object in a spatially sampling manner, the polarization direction indicating the fiber direction of the carbon fiber material; and
  positioning the test object and another test object next to each other depending on position information on a position of the test object relative to the polarization-sensitive camera and the fiber direction of the carbon fiber material of the test object, so that in an adjoined state the fiber direction of the carbon fiber material of the test object and a fiber direction of a carbon fiber material of the another test object are in a predetermined orientation with respect to each other.

14. A non-transitory computer readable medium including a computer program for executing, when the program is executed on a computer, a method for measuring fiber direction, the method comprising:
  illuminating carbon fiber material of a test object; and
  detecting, by a polarization-sensitive camera, a polarization direction of light reflected by the test object in a spatially sampling manner, the polarization direction indicating the fiber direction of the carbon fiber material; and
  positioning the test object and another test object next to each other depending on position information on a position of the test object relative to the polarization-sensitive camera and the fiber direction of the carbon fiber material of the test object, so that in an adjoined state the fiber direction of the carbon fiber material of the test object and a fiber direction of a carbon fiber material of the another test object are in a predetermined orientation with respect to each other.

* * * * *